(12) United States Patent
Wolleschensky et al.

(10) Patent No.: US 7,605,976 B1
(45) Date of Patent: Oct. 20, 2009

(54) METHOD AND DEVICE FOR CHANGING LIGHT IN AN ADJUSTABLE MANNER

(75) Inventors: Ralf Wolleschensky, Apolda (DE);
Michael Kempe, Jena (DE); Peter Klopfleisch, Jena (DE)

(73) Assignee: Carl Zeiss Microimaging GmbH, Jena (DE)

( * ) Notice: Subject to any disclaimer, the term of this patent is extended or adjusted under 35 U.S.C. 154(b) by 273 days.

(21) Appl. No.: 11/416,455

(22) Filed: May 3, 2006

(30) Foreign Application Priority Data

May 3, 2005 (DE) .................... 10 2005 020 543

(51) Int. Cl.
*G02B 21/06* (2006.01)
(52) U.S. Cl. .................... 359/386; 359/385; 359/495
(58) Field of Classification Search .................... None
See application file for complete search history.

(56) References Cited

U.S. PATENT DOCUMENTS

| | | | |
|---|---|---|---|
| 6,167,173 A | 12/2000 | Schoeppe et al. | |
| 6,377,344 B2 | 4/2002 | Schoeppe et al. | |
| 6,510,001 B1 | 1/2003 | Engelhardt et al. | |
| 6,654,165 B2 | 11/2003 | Engelhardt et al. | |
| 6,809,324 B1 | 10/2004 | Schmidt | |
| 6,867,919 B2 * | 3/2005 | Seyfried | 359/618 |
| 6,891,613 B2 | 5/2005 | Wolleschensky et al. | |
| 6,947,127 B2 | 9/2005 | Kempe | |
| 7,009,763 B1 | 3/2006 | Wolleschensky | |
| 2003/0133189 A1 | 7/2003 | Engelhardt et al. | |
| 2004/0159797 A1 | 8/2004 | Wolleschensky | |
| 2004/0174585 A1 | 9/2004 | Birk | |

FOREIGN PATENT DOCUMENTS

| | | |
|---|---|---|
| DE | 19702753 | 7/1998 |
| DE | 19842288 | 2/2000 |
| DE | 19936573 | 2/2001 |
| DE | 10033180 | 5/2002 |
| DE | 10137155 | 2/2003 |
| DE | 10257237 | 6/2003 |
| DE | 10241472 | 3/2004 |
| EP | 1353209 | 10/2003 |

* cited by examiner

*Primary Examiner*—Arnel C Lavarias
(74) *Attorney, Agent, or Firm*—Jacobson Holman PLLC

(57) ABSTRACT

Method and device for changing the illumination light and/or specimen light with respect to its spectral composition and/or intensity in an adjustable manner, wherein a spatial separation into the radiation components of different polarization is carried out with the first polarization means (Pol 1), a spectral spatial splitting of at least one radiation component is carried out with the first dispersion means (Disp1), and the polarization state of at least one part of the spectrally spatially split radiation component is changed, wherein a reflection of the illumination light and/or the detection light is carried out.

6 Claims, 13 Drawing Sheets

State of the art

METHOD AND DEVICE FOR CHANGING LIGHT IN AN ADJUSTABLE MANNER

BACKGROUND OF THE INVENTION

1. Field of the Invention

The invention relates to a method and arrangements in microscopy, in particular fluorescence microscopy, laser scanning microscopy, fluorescence correlation spectroscopy and near-field scanning microscopy, for examining predominantly biological specimens, preparations and related components. This includes methods for screening active ingredients based on fluorescence detection (high throughput screening) as well as methods of flow cytometry. Therefore, simultaneous examinations of specimens with multiple fluorophores in real time by means of simultaneous illumination of the specimen at multiple sampling points are possible with overlapping fluorescence spectra even in three dimensional structures of thick specimens.

2. Related Art

A typical field of application of light microscopy for examining biological preparations is fluorescence microscopy (literature: Pawley, *Handbook of Biological Confocal Microscopy*, Plenum Press, 1995). In this case, specific dyes are used for specific labeling of cell parts.

The beamed-in photons having a determined energy excite the dyed molecules, through the absorption of a photon, from the original state into an excited state. This excitation is usually referred to as single photon absorption. The dyed molecules that are excited in this way can return to the original state in various ways. In fluorescence microscopy the most important way is the transition with emission of a fluorescence photon. The wavelength of the emitted photon is generally red-shifted, thus has a longer wavelength. The Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, several parts of a preparation can also be dyed simultaneously with different dyes that bind in a specific manner (multiple fluorescence). Special dichroic beam splitters are used in turn to distinguish the fluorescence signals, emitted by the individual dyes.

In addition to excitation of dyed molecules with a high-energy photon (single photon absorption), excitation with a plurality of low-energy photons is also possible. The sum of energies of the single photons is equal to approximately a multiple of the high-energy photon. This type of excitation of dyes is known as multiphoton absorption (literature: Corle, Kino. *Confocal Scanning Optical Microscopy and Related Imaging Systems*. Academic Press, 1996). However, the dye emission is not influenced by this type of excitation. That is, the emission spectrum undergoes a negative Stokes shift in multiphoton absorption; thus, it has a shorter wavelength compared to the excitation radiation. The separation of the excitation radiation from the emission radiation is carried out in the same way as in single photon absorption.

The prior art shall be explained below in detail by way of example with reference to a confocal laser scanning microscope (LSM) (FIG. 1).

An LSM is essentially composed of four modules: light source, scan module, detection unit and microscope. These modules are described below in detail. In addition, reference is made to DE 19702753 A1.

Lasers with different wavelengths are used in an LSM for specific excitation of different dyes in a preparation. The choice of excitation wavelengths is governed by the absorption characteristics of the dyes to be examined. The excitation radiation is generated in the light source module. Various lasers (for example, argon, argon/krypton, solid state lasers, TiSa lasers, diodes) are used for this purpose. Furthermore, the selection of wavelengths and the adjustment of the intensity of the required excitation wavelength are carried out in the light source module, i.e., using an acousto-optic crystal. The laser radiation subsequently reaches the scan module via a fiber or a suitable mirror arrangement.

The laser radiation, generated in the light source, is focused in the preparation in a diffraction-limited manner by means of the objective via the scanners, scanning optics and tube lens. The scanner is moved over the specimen point-by-point in x-y direction. The pixel dwell times when scanning over the specimen are mostly in the range of less than one microsecond to several seconds.

In confocal detection (descanned detection) of the fluorescent light, the light, which is emitted from the focal plane (specimen) and from the planes located above and below the latter, reaches a dichroic beam splitter (MDB) via the scanners. This dichroic beam splitter separates the fluorescent light from the excitation light. The fluorescent light is subsequently focused on a diaphragm (confocal diaphragm/pinhole), which is located precisely in a plane conjugate to the focal plane. In this way, fluorescent light components outside of the focus area are suppressed. The optical resolution of the microscope can be adjusted by varying the size of the diaphragm. Another dichroic blocking filter (EF), which again suppresses the excitation radiation, is located behind the diaphragm. After passing the blocking filter, the fluorescent light is measured by means of a point detector (PMT).

When using multiphoton absorption, the excitation of the dye fluorescence is carried out in a small volume, at which the excitation intensity is particularly high. This area is only negligibly larger than the detected area when using a confocal arrangement. Hence, there is no need to use a confocal diaphragm; and the detection can be carried out directly after the objective (non-descanned detection).

In another arrangement for detecting a dye fluorescence excited by multiphoton absorption, descanned detection is carried out again, but this time the pupil of the objective is imaged in the detection unit (non-confocal descanned detection).

From a three dimensionally illuminated image, only the plane (optical section), which is located in the focal plane of the objective, is reproduced by the two detection arrangements in connection with the corresponding single photon absorption or multiphoton absorption. By recording a plurality of optical sections in the x-y plane at different depths z of the specimen, a three dimensional image of the specimen can be generated then in a computer-assisted manner.

Therefore, the LSM is suitable for examining thick preparations. The excitation wavelengths are determined by the utilized dye with its specific absorption characteristics. Dichroic filters, adapted to the emission characteristics of the dye, ensure that only the fluorescent light, emitted by the respective dye, will be measured by the point detector.

Currently in biomedical applications a number of different cell regions are labeled simultaneously with different dyes (multifluorescence). In the prior art the individual dyes can be detected separately based on either different absorption characteristics or emission characteristics (spectra).

For separate detection, an additional splitting of the fluorescent light of a plurality of dyes is carried out with the secondary beam splitters (DBS); and a separate detection of the individual dye emissions is carried out in various point detectors (PMT 1-4).

Flow cytometers are used for examining and classifying cells and other particles. For this purpose the cells are dissolved in a liquid and are pumped through a capillary. In order to examine the cells, a laser beam is focused in the capillary from the side. The cells are dyed with different dyes or fluorescing biomolecules. The excited fluorescent light and the backscattered excitation light are measured. The fluorescence signal of the specimen is separated from the excitation light by means of dichroic beam splitters (MDB, see FIG. 1).

The size of the cells can be determined from the backscattered signal. Different cells can be separated/sorted or counted separately by means of the spectral characteristics of the fluorescence of individual cells. The sorting of the cells is carried out with an electrostatic field in different capillaries. The results, that is, for example, the quantity of cells with dye A in comparison to cells with dye B, are often displayed in histograms.

The flow rate is typically about 10 to 100 cm/s. Therefore, a highly sensitive detection is necessary. According to the prior art, a confocal detection is carried out in order to limit the detection volume.

According to the prior art, so-called line scanners are also used, instead of point scanners (literature: Corle, Kino. *Confocal Scanning Optical Microscopy and Related Imaging Systems*. Academic Press, 1996). The basic construction corresponds in essence to that of an LSM, according to FIG. 1. However, instead of a point focus, a line is imaged in the specimen; and the specimen to be examined is scanned in only one direction (x or y). The image acquisition rate can be significantly increased by scanning a line, instead of a point. Therefore, this scanning method can be used for observing high speed processes in real time (real time microscopy).

In another arrangement for real time microscopy, according to the prior art, the entire field to be examined is illuminated by an expanded light source. However, only special point patterns of the total field to be scanned are uncovered by a rapidly rotating disk. These methods are usually referred to in the literature as the Nipkow disk methods (literature: Corle, Kino. *Confocal Scanning Optical Microscopy and Related Imaging Systems*. Academic Press, 1996).

Arrangements for screening dyes, such as in so-called chip readers, are similar in their optical construction to a laser scanning microscope. However, they scan a significantly larger image field for examining macroscopic specimens, for example, screening of active ingredients on a biochip. The edge length of the scan fields amounts to several 10 mm. These scan fields can be achieved, e.g. by increasing the scan angles of the galvoscanners, by arranging the specimen in an intermediate image of the microscope arrangement or by a special objective arrangement (macro-objective), which images the intermediate image on the specimen in a magnified manner.

According to the prior art, the separation of the excitation light from the light, emitted by the specimen, is carried out by spectral separation using the Stokes shift by restricting the numerical aperture of the optics used for specimen illumination and detection or by splitting into different polarization directions.

Special dichroic beam splitters are used for the spectral separation of the excitation light from the light, emitted by the specimen. As shown in FIG. 2*a*, these dichroic beam splitters are usually constructed in such a way that they reflect the excitation light as efficiently as possible and transmit the light, emitted by the specimen, as efficiently as possible. The reflection factor (reflectivity) is shown as a function of the wavelength. When using polarized excitation light, the minimum spectral bandwidth (s) of the reflected wavelength range is about 10 nm; the edge steepness (f) is usually greater than 5 nm. Therefore, according to the prior art, the light, emitted by the specimen, can be efficiently separated with a dichroic beam splitter when using an excitation wavelength. However, the efficiency decreases when a plurality of dyes with a plurality of wavelengths are excited simultaneously (multifluorescence microscopy), since a spectral overlapping of the excitation light and the emitted light usually occurs. Furthermore, a special beam splitter must be created each time when using different dyes with different absorption characteristics. In a wide field microscope, there is usually a broadband excitation of the specimen with light from a white light source with partial spectral overlapping of the excitation radiation and emitted radiation. Hence, the use of dichroic beam splitters, according to the prior art, results in poor efficiency of the separation of the excitation light from the emitted light.

The separation of excitation light from emitted light by restricting the numerical aperture of the specimen illumination optics (4 in FIG. 2*b*) can be carried out, for example, by illuminating the specimen with a restricted aperture, so that only the near-axis beams (1) arrive in the direction of the specimen (2). Since the emission is carried out in all spatial directions, this light from the specimen (2) can be collected in the rest of the aperture area. The separation of the excitation light from the emitted light is carried out subsequently by a partially fully reflecting (black area) plane plate (3). The detection of the light emitted by the specimen is carried out in the beam direction (5). The drawback with the methods for dividing the numerical aperture, known from the prior art (e.g. EP 1353209), is that, on the one hand, the efficiency of detection and, on the other hand, the optical resolution of the arrangement decreases due to the restriction of the aperture. These two parameters are connected in this regard. For example, in order to achieve a highly efficient separation, the optical resolution decreases.

The drawback with all of the methods, according to the prior art, is that the separation of the excitation light from the light, emitted by the specimen, is carried out in a wavelength-dependent manner, i.e. not flexibly adjustable, or with a limited efficiency of typically 70% to 90%, depending on the required spectral characteristics and the quantity of illumination lines.

U.S. Pat. No. 6,510,001, U.S. Pat. No. 6,654,165, US 2003/0133189 and DE 19936573 disclose optical devices, where a spectrally flexible separation of the detection light from the excitation light can be carried out in an adjustable manner without any movement of mechanical components. In this arrangement, and with reference to FIG. 3 of these documents, the MDB is replaced by an acousto-optic modulator AOTF (19, 4). It transmits the viewing light (5, 12), coming from the direction of the specimen, so that it arrives in the direction of the detector (15). The excitation light (3, 9) runs at an angle relative to (12) and is diffracted into the joint specimen beam path (5) by means of the AOTF. Therefore, the frequency of the AOTF must be adjusted in such a manner that the excitation beam path and the detection beam path run collinearly. If this is not guaranteed, then the result is a reduction in the detection efficiency, particularly in the case of a confocal detection, and/or aliasing errors, because when different wavelengths are used, the excitation spots are not stacked. Special compensation devices are described in DE 10137155. The drawback of these arrangements lies in the need for a plurality of tunable optical components that have a negative impact on the overall transmission.

The DE 10257237 discloses a method and optical devices, with which an achromatic separation of the detection light from the excitation light can be carried out in a wide field or in a line-scanning microscope. In this case the light radiation, which is excited in a specimen and/or which is backscattered and/or reflected by the specimen, is separated by focusing the specimen illumination in and/or in the vicinity of a pupil plane of the beam path between the specimen plane and the acquisition plane, and by providing means for a spatial separation of the illumination light from the detection light in this plane.

FIG. 3 of DE 10241472 discloses a method and arrangement for changing the spectral composition and/or the intensity of the illumination light and/or the specimen light in an adjustable manner. Therefore (referring to FIG. 4 of DE 10241472), a spatial separation into radiation components of different polarization is carried out with the first polarization means (P1, P3); a spectral, spatial splitting of at least one radiation component is carried out with the first dispersion means (D1); the spectrally spatially split components are imaged (L1) on an element S; the polarization state of at least one part of the spectrally spatially split radiation component is changed by the action of the element S; and a spatial separation and/or combination of radiation components of different polarization are/is carried out by the second imaging means (L2) and the polarization means (P2, P4). In this respect a spatial combination of radiation components, which are changed and not changed with respect to their polarization state, is advantageously carried out by the second dispersion means (D2). The drawback with this arrangement lies in the number of optical components for a spectral spatial splitting, by means of which the efficiency of the arrangement is reduced. Furthermore, the manipulation of the polarization state of the spectral components at the element S is carried out with a linear array. Depending on the specified spectral resolution, this array is costly with regard to the electronic wiring. In addition, the speed is restricted when using a spatial light modulator and amounts to several 10 ms. In the prior art DE 10241472 (FIG. 3), dispersive elements (e.g. prisms or gratings) D1 and D2, which split the light radiation spatially and spectrally along the Y coordinate and combine it again, are disposed between two beam splitter cubes each (P2 and P1 or P4 and P3). The optics L1 and L2 are positioned at a distance from their respective focal lengths f, which can also vary for the optics, between the dispersive elements D1 or D2 and an element for rotating the polarization, for example a spatial light modulator (SLM) S. The optics L1 and L2 together with the dispersive elements D1 and D2 are used to produce a spectral Fourier plane at the location of the SLM S. In this plane the spectral components of the light, coming from the direction 2 or the direction 1, are separated spatially along the Y coordinate. The SLM (e.g. SLM640 of the company Jenoptik, Germany) comprises a number of strips (in the case of the SLM 640 there are 640 strips), which can be actively controlled individually. Depending on the active control of the respective pixel, the polarization direction of the light passing through can be varied. The SLMs, according to the prior art, are installed in so-called pulse shapers (literature: Stobrawa et al. *Applied Physics* B72, pp. 627-630 (2002)). Therefore, the action of the SLM in combination with the dispersive elements results in a phase delay and/or a change in the amplitude of the spectral components of the light source. In addition, in contrast to the arrangements described below, the light source must be polarized linearly, because otherwise an energy loss occurs. The DE 19842288 discloses an arrangement, which selectively reflects the spectrally split illumination light over a mirror mounting (ST) and combines it again in the dispersive element. The specimen light is also split spatially and spectrally by means of the dispersive element and then deflected into the other corresponding separate detection channels by means of special wedge-shaped glass prisms (GK). Owing to the horizontal wedge shift, the channel position is changed; and owing to the vertical wedge shift, the bandwidth is changed. This alternative has advantages in comparison to the above-described arrangements. Nevertheless, the mirror system (ST, GK) and its actuation are complicated and exhibits only limited flexibility. In particular, the channel splitting of the specimen light is carried out in a manner that is determined by the number and shape of the glass wedges.

SUMMARY OF THE INVENTION

In accordance with the present invention, a method and a device are provided for changing the illumination light and/or specimen light with respect to its spectral composition and/or intensity in an adjustable manner, wherein a spatial separation into the radiation components of different polarization is carried out with the first polarization means (Pol 1), a spectral spatial splitting of at least one radiation component is carried out with the first dispersion means (Disp1), and the polarization state of at least one part of the spectrally spatially split radiation component is changed, wherein a reflection of the illumination light and/or the detection light is carried out.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
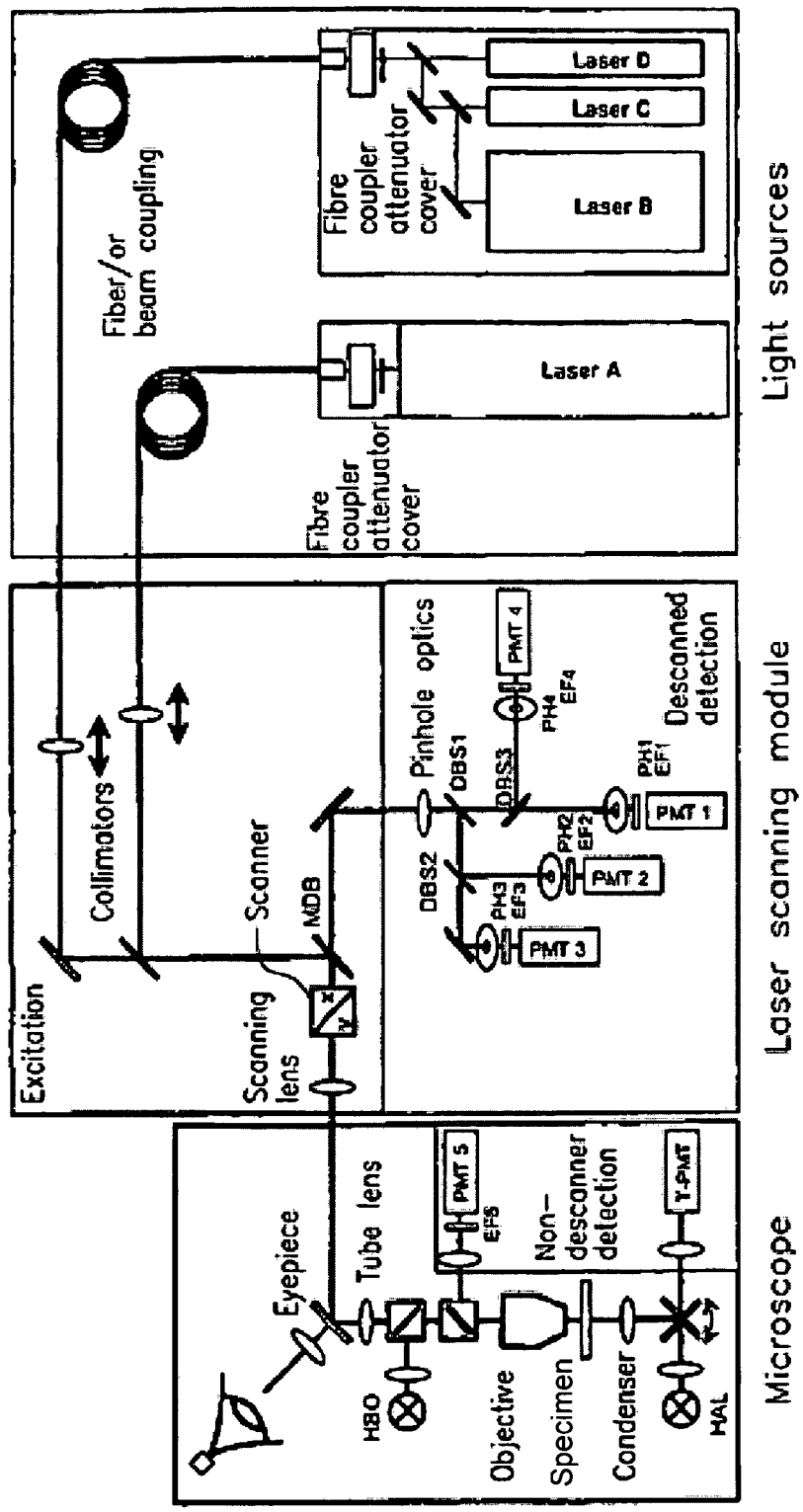
FIG. 1 is a schematic drawing of a prior art confocal laser scanning microscope.
Figure 2:
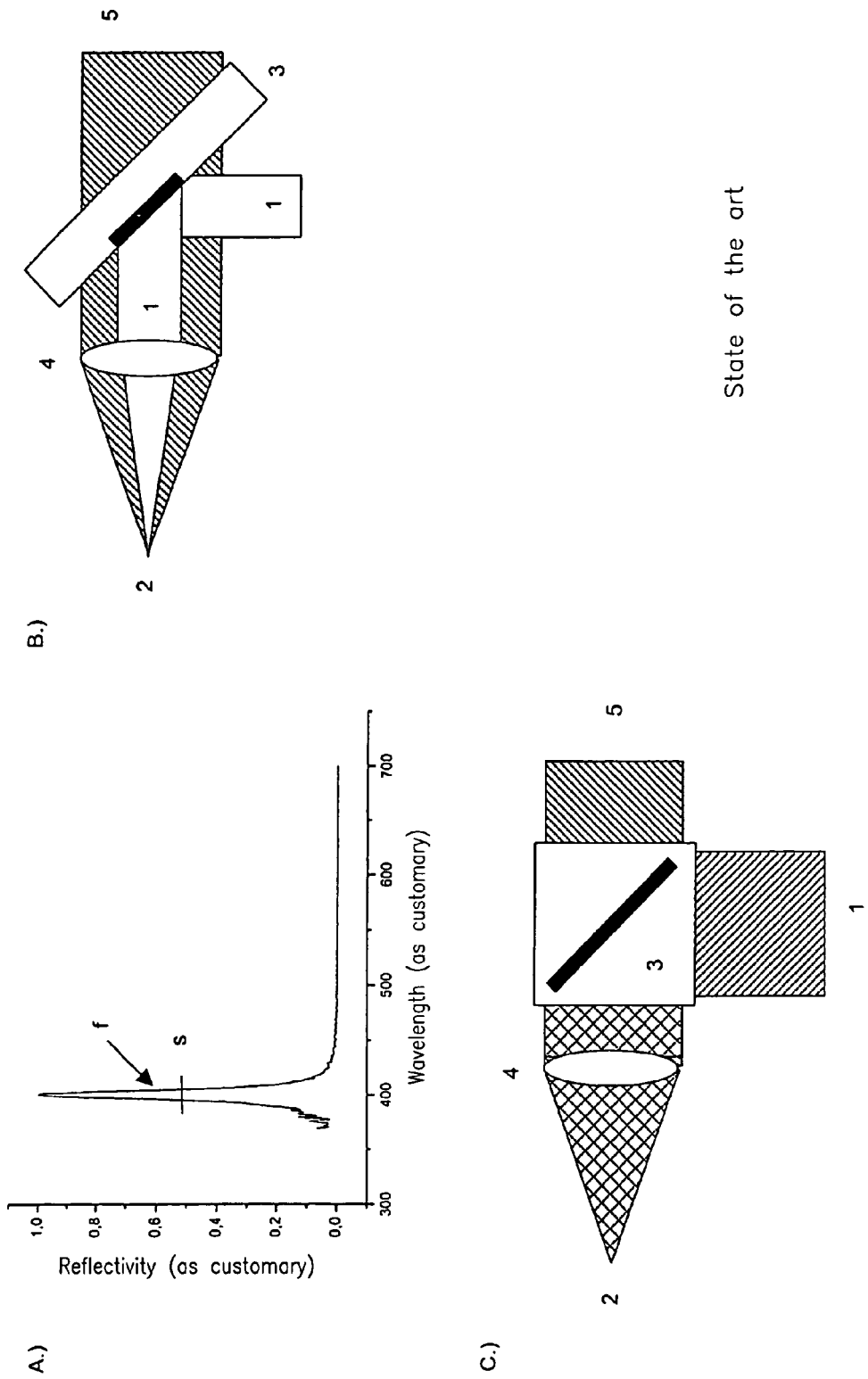
FIG. 2A is a graph in which the reflection factor (reflectivity) of a dichroic beam splitter of a prior art LSM is shown as a function of the wavelength.
FIGS. 2B and 2C are cross-sectional representations of the separation of excitation light from emitted light in the specimen illumination optics of a prior art LSM.
Figure 3:
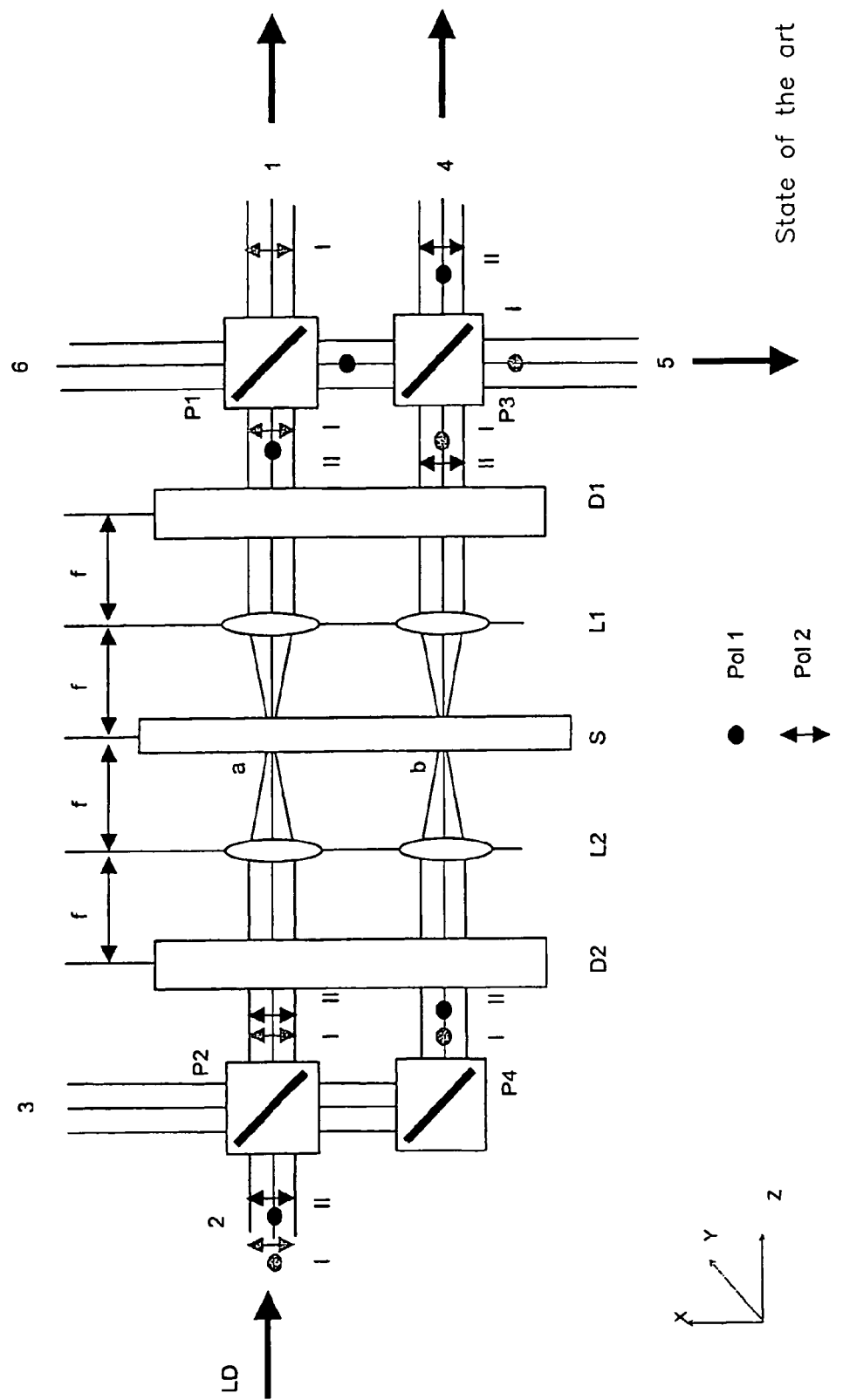
FIG. 3 is a schematic drawing of the optical device disclosed in DE 10241472 for changing the spectral composition and/or the intensity of the illumination light and/or the specimen light in an adjustable manner.
Figure 4:
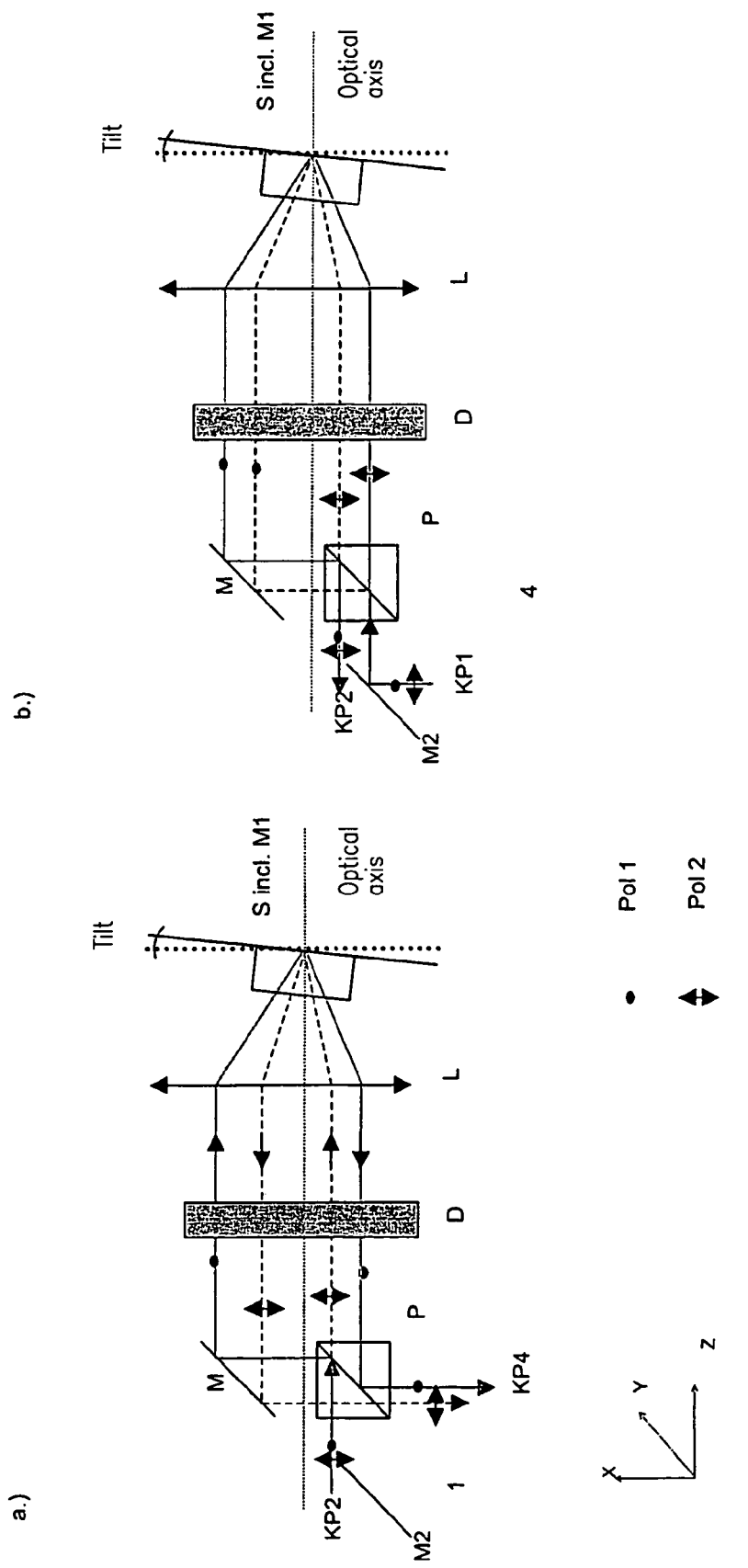
FIGS. 4A and 4B are schematic drawings showing a device in accordance with the present invention for changing light in an adjustable manner, in reflection.

FIG. 4 shows the inventive arrangement in reflection.

In FIG. 4a, an essentially unpolarized light from the specimen reaches a polarizing beam splitter P by way of a coupling port KP 2, is split by this polarizing beam splitter into perpendicular polarization components (arrows or dots). In this respect, one component reaches directly a dispersive element D; and the other component is mirrored at the splitter P and reaches the element D by way of a mirror M and is split spectrally at said element.

The radiation is focused on the SLM S and the mirror M1 in the plane S/M1 by means of a lens L; and, thus, its polarization can be affected in a number of ways as a function of the wavelength. Hence, the polarization of the individual spectral components of the light, which arrive again in the direction of the polarizing beam splitter P, can be varied. The SLM can comprise actively controlled liquid crystal cells.

In the plane of the SLM S, the polarization of the individual or several spectral components can be affected in such a manner that the polarization plane is rotated by exactly 90 deg. or a value diverging from 90 deg. In addition, it is possible to switch the SLM S in such a manner that the polarization plane remains unaffected by the spectral components. For this purpose the SLM (spatial light modulator) (the backside of the SLM is reflecting), which influences the spectrally split ray components, reflected at the mirror M1, is mounted on a mirror M1, which is tilted at an angle ε.

In the illustrated case, there is no affect on the specimen light in a potential design. It arrives unaffected in the direction of detection, where other means for spectral, separated detection can be provided (DE 10033180 A). Detection can be carried out in a descanned, partially descanned or non-descanned manner.

The reflected components arrive again by way of the dispersive element, are combined there and arrive by way of the mirror M or the backside of the polarizing beam splitter P at the coupling port KP 4 (at a variety of spots). Otherwise, reference is made to DE 10241472 A1.

FIG. 4b discloses the influence on the illumination light, which reaches the polarizing beam splitter P by way of the coupling port KP1 and a mirror M2, is split into the two polarization components, and arrives in the direction of the coupling port KP2 by way of the dispersive element D, lens L and the SLM/mirror M1.

A variety of polarization directions reach different spots of the dispersive element and the SLM and can, therefore, be affected by the SLM in different ways, before they are combined again by the splitter P in KP2.

Therefore, the polarization plane of the components of the illumination light, adjustable by means of the SLM, is rotated in the respective perpendicular direction. These components are combined again (in the direction of the specimen) after the polarizing beam splitter P.

Figure 5:
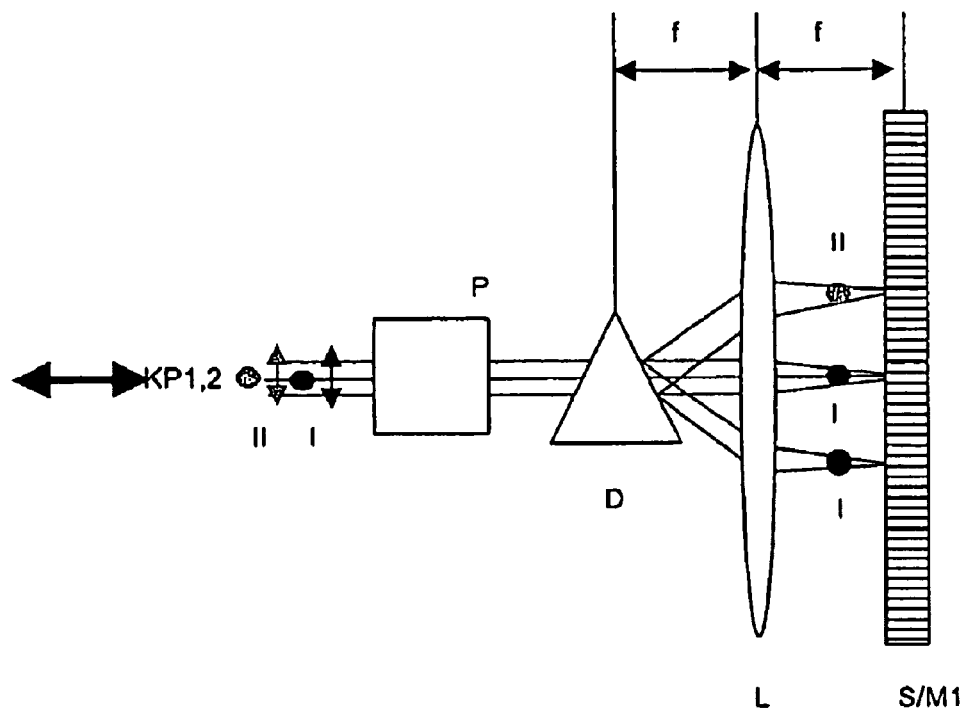
FIG. 5 is a side view of the device in accordance with the present invention.

FIG. 5 depicts a detail of the inventive arrangement from the side, whereby light having a plurality of wavelengths I and II with different polarization directions is shown. Owing to the separation at the element D, the excitation light or the detection light can be affected at the SLM in a number of ways by rotating the polarization and can be deflected to various outlets or totally or partially masked out.

Figure 6:
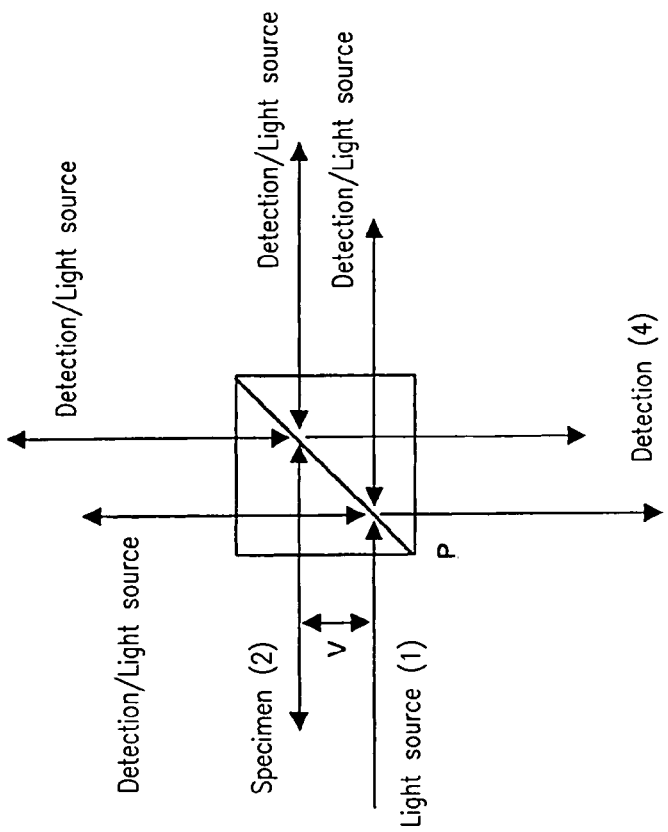
FIG. 6A is a schematic drawing showing the beam path at the polarization splitter without tilting the mirror M1 in the device in accordance with the present invention.
FIG. 6B is a schematic drawing showing the beam path at the polarization splitter with the mirror M1 tilted by $\epsilon$ in the device in accordance with the present invention.
Figure 6:
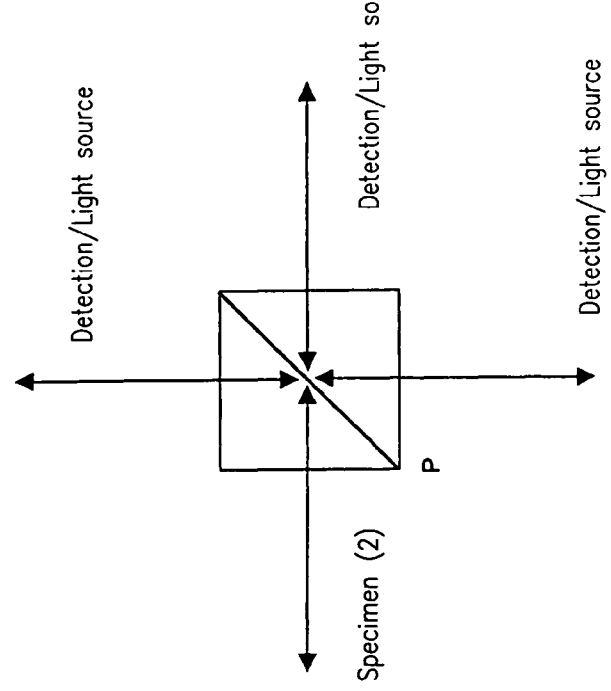

FIG. 6 shows the difference between the beam paths with or without tilting the mirror M1. It is clear that tilting the mirror M1 (see FIG. 6b) results in a shift V of the light paths of the light source (1) and the specimen light (2) at the polarizing beam splitter P. Furthermore, the detection (4) is separated. The three ports (KP1, KP2, and KP4) are needed so that in a fluorescence microscope the excitation light, guided from the direction (1) coming in the direction of the specimen (2) and the specimen light from (2) coming in the direction of the detection (4) can be separated. This is not possible without tilting M1, because the ports (2) and (1) form a common beam path. Therefore, a bundling of the excitation light into the specimen is not possible (see FIG. 6a).

Figure 7:
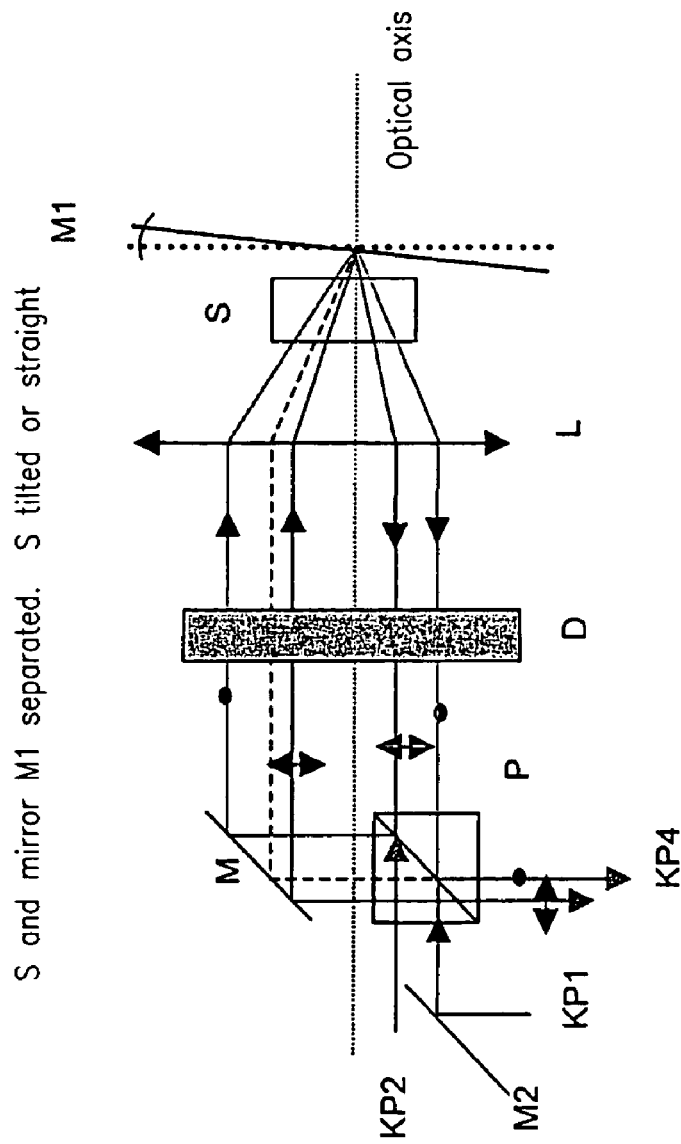
FIG. 7 is a schematic drawing showing an arrangement where the SLM element S is arranged separately at a distance from the mirror M1, and where the element S is tilted or straight.

FIG. 7 shows an arrangement, where the SLM S is arranged separately at a distance from the mirror M1.

Figure 8:
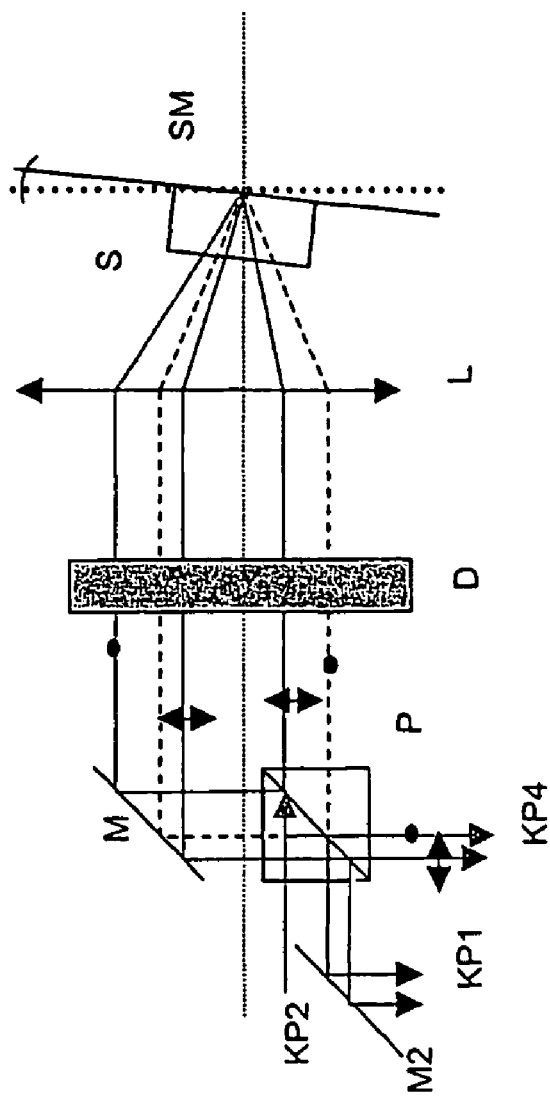
FIG. 8 is a schematic drawing shows the element S, in which the backside of element S has a mirror and the front side has a mirror mask SM.

FIG. 8 shows a mirror mask SM, following the SLM, which is shown as a detail in FIG. 9a. It exhibits reflecting and non-reflecting segments (dark segments AA non-reflecting).

FIG. 9b is a partial sectional view of such a mirror mask, which exhibits advantageously three layers at non-reflecting areas, whereby the layer c is reflecting, b is a layer for polarization rotation (lambda quarter plate), and a is transmissive in the dark segments AA.

Thus, the radiation undergoes a polarization rotation at the transmissive spots of SM. If SM is shifted (vertically) along X, the spatially different transparent areas arrive in the spectrally split light path, thus affecting other wavelength components. Thus, SM acts as an adjustable reflector by rotating the polarization for specific spectral components in specific areas.

The SM affects in an advantageous manner the illumination light, adjustable in its spectral composition.

Figure 10:
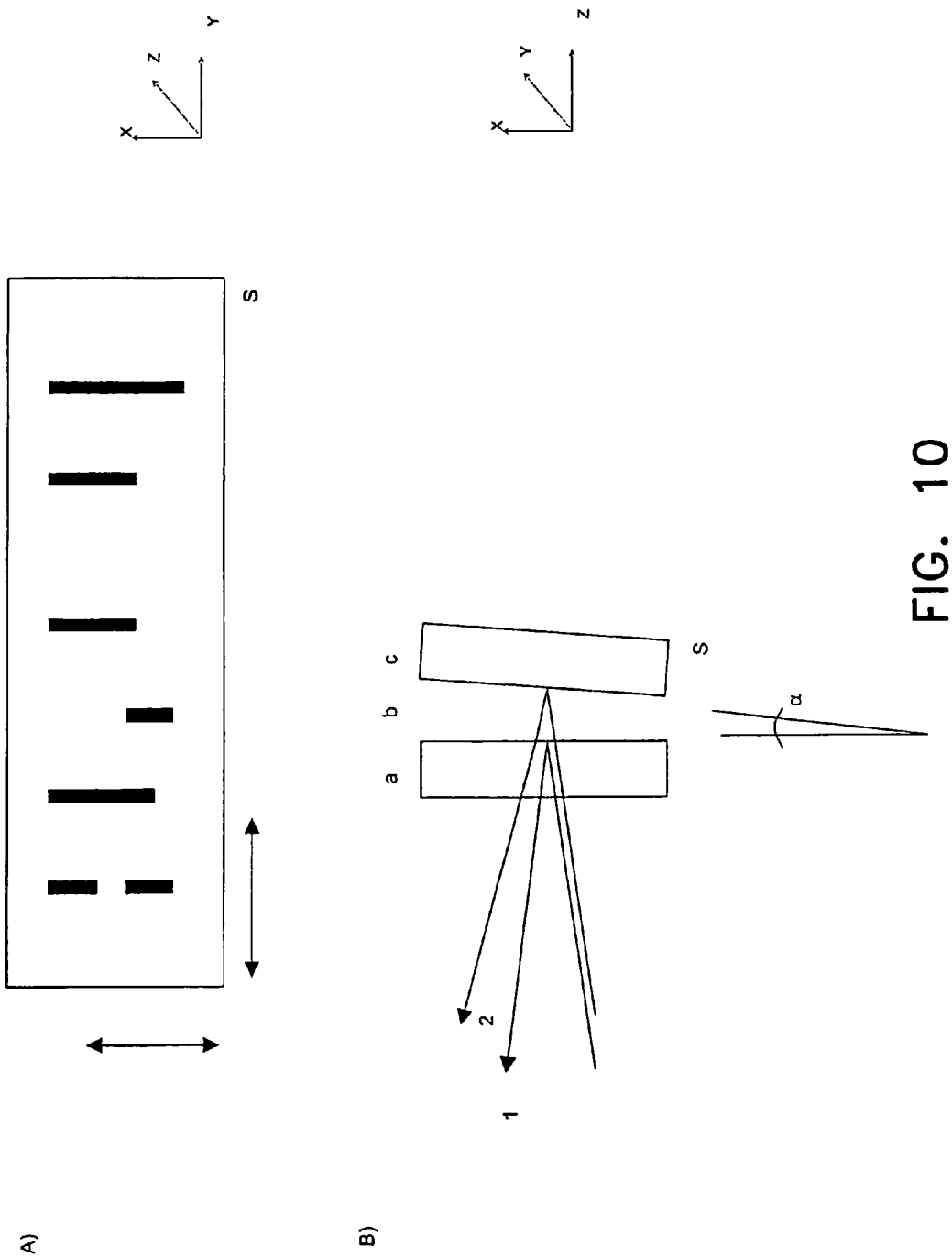
FIG. 10A is an enlarged view of another embodiment of a mirror mask SM.
FIG. 10B is a partial sectional view of the mirror mask SM of FIG. 10A.

Another embodiment of the element SM is depicted in FIG. 10. In this case the layer a with the mirror mask and the reflecting layer c are tilted at a small angle α in opposite directions. In this way light beams, which pass through the mask and are reflected by the layer c, undergo an angle shift of 2α in relation to beams, reflected by the layer a. The layer b does not exhibit any polarization-optic characteristics and can, therefore, be either air or a medium that is adapted in an advantageous manner with respect to the refractive index (to avoid losses due to undesired interface reflections) to the substrate of the mirror mask a.

Figure 11:
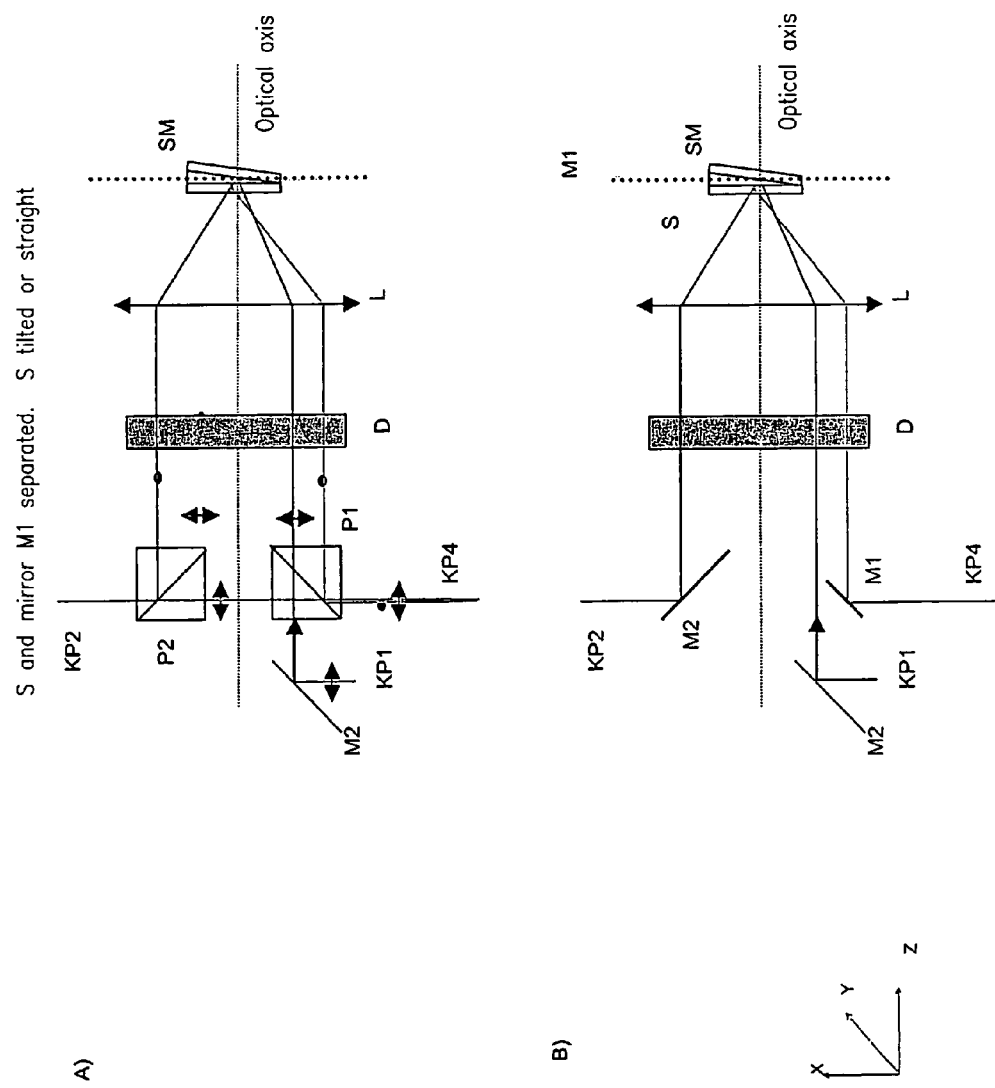
FIG. 11A is a schematic drawing showing an arrangement using the mirror mask SM of FIG. 10 in which the element S and the mirror M1 are separated, the element S can be tilted or straight, and two polarization beam splitters P1 and P2 are used.
FIG. 11B is a schematic drawing showing an arrangement using the mirror mask SM of FIG. 10 in which the element S and the mirror M1 are separated, the element S can be tilted or straight, and two mirrors M1 and M2 are used.

FIG. 11 depicts two arrangements, using the element SM from FIG. 10. In this case all elements with functions or descriptions analogous to those in the preceding figures are labeled the same way. FIG. 11a depicts an alternative with polarization-optic elements, in which case two polarization beam splitters P1 and P2 are used now. The advantage of this arrangement is that a polarization direction of the light (KP2), emitted by the specimen, reaches the detection port KP4 directly via P2 and P1, thus minimizing the losses for this light. The separation of the excitation from the detection for the other polarization direction (polarized parallel to the excitation light) is carried out via the spectrally dependent tilting of the light beam at SM. Excitation light, rotated in its polarization direction due to multiscattering at the specimen, also arrives in KP4 via P2 and P1. This, in general, very small, component of the excitation light has to be blocked, prior to detection, by filters, when fluorescence imaging occurs. On the other hand, this light enables imaging in incident light (scattered light), if a corresponding blocking is omitted. The geometric separation of the excitation from the detection also allows a design as shown in FIG. 11B, which is not based on polarization-optic components. In this case P1 and P2 are replaced by mirrors M1 and M2. Therefore, the separation is independent of the polarization of the light (and thus also the optionally present rotation of the polarization of the excitation light due to scattering). In addition, it simplifies the construction due to the use of simpler components.

Figure 9:
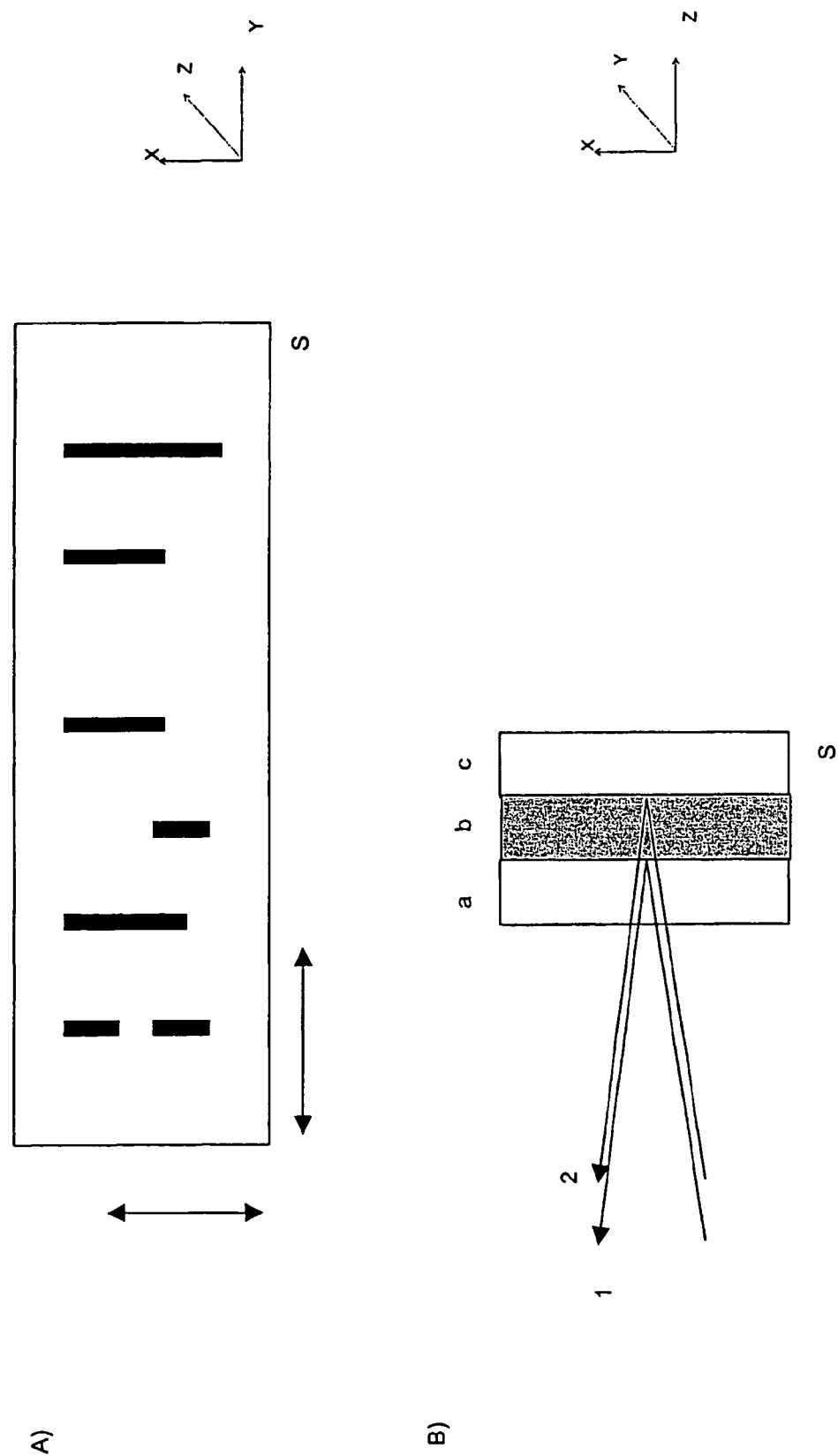
FIG. 9a is an enlarged view of the mirror mask SM of FIG. 8.
FIG. 9b is a partial sectional view of the mirror mask SM of FIG. 8.
Figure 12:
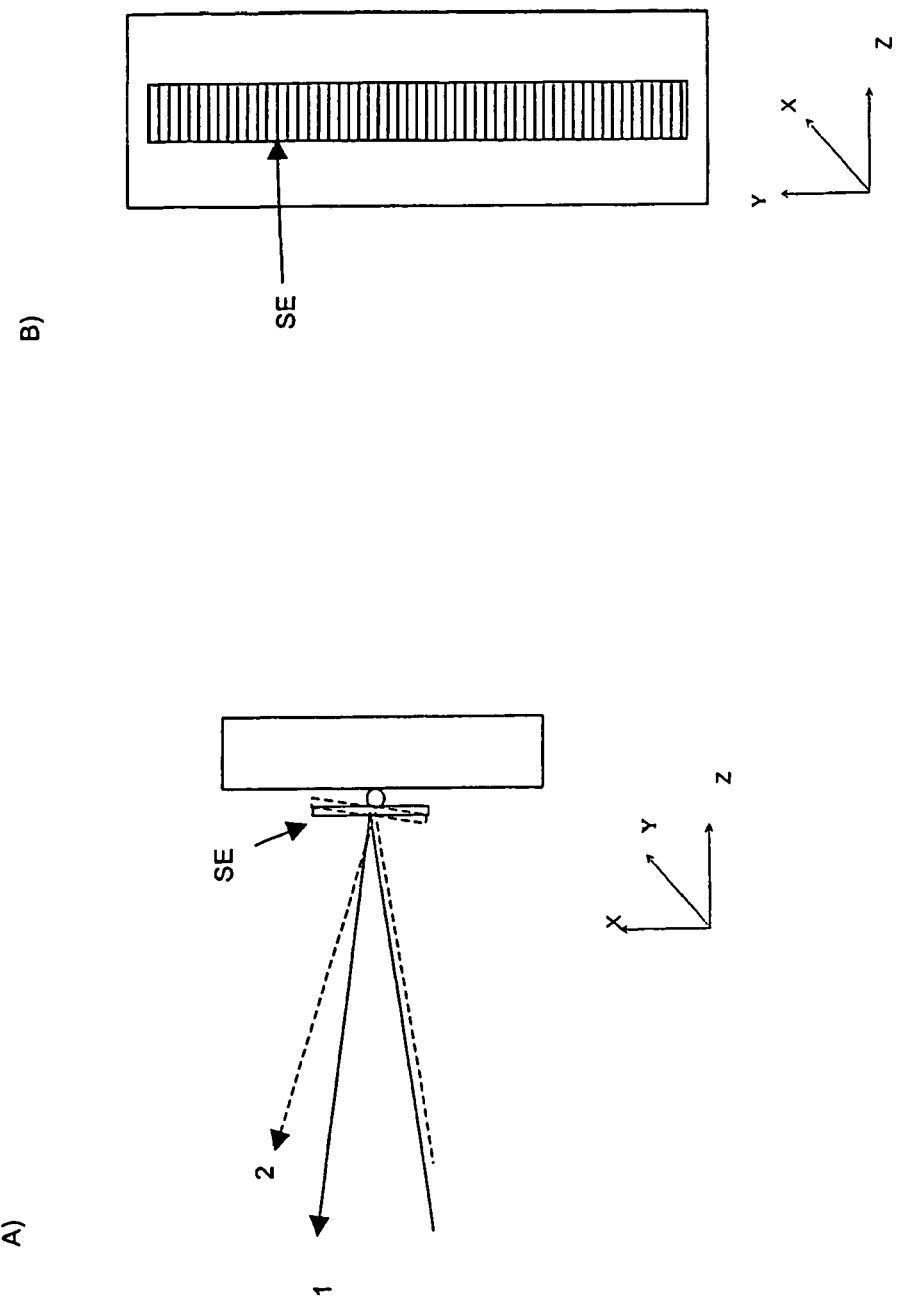
FIGS. 12A and 12B are schematic side and front views showing a mirror array for use in the arrangements of FIGS. 11A and 11B instead of the mirror mask SM as shown in FIGS. 9A, 9B, 10A, and 10B.

Instead of the element SM, as depicted in FIGS. 9 and 10, a mirror array, as shown as a schematic drawing in FIG. 12, can also be used in the configurations in FIG. 11. In this case every small mirror element SE can be tilted individually into at least two discrete positions, so that a beam is deflected either as 1 or 2, depending on the position along the Y axis on which it falls on the SM. Therefore, the size of the mirror ought to be adapted to the resolution of the dispersive element and the subsequent optics in order to enable total flexibility.

Figure 13:
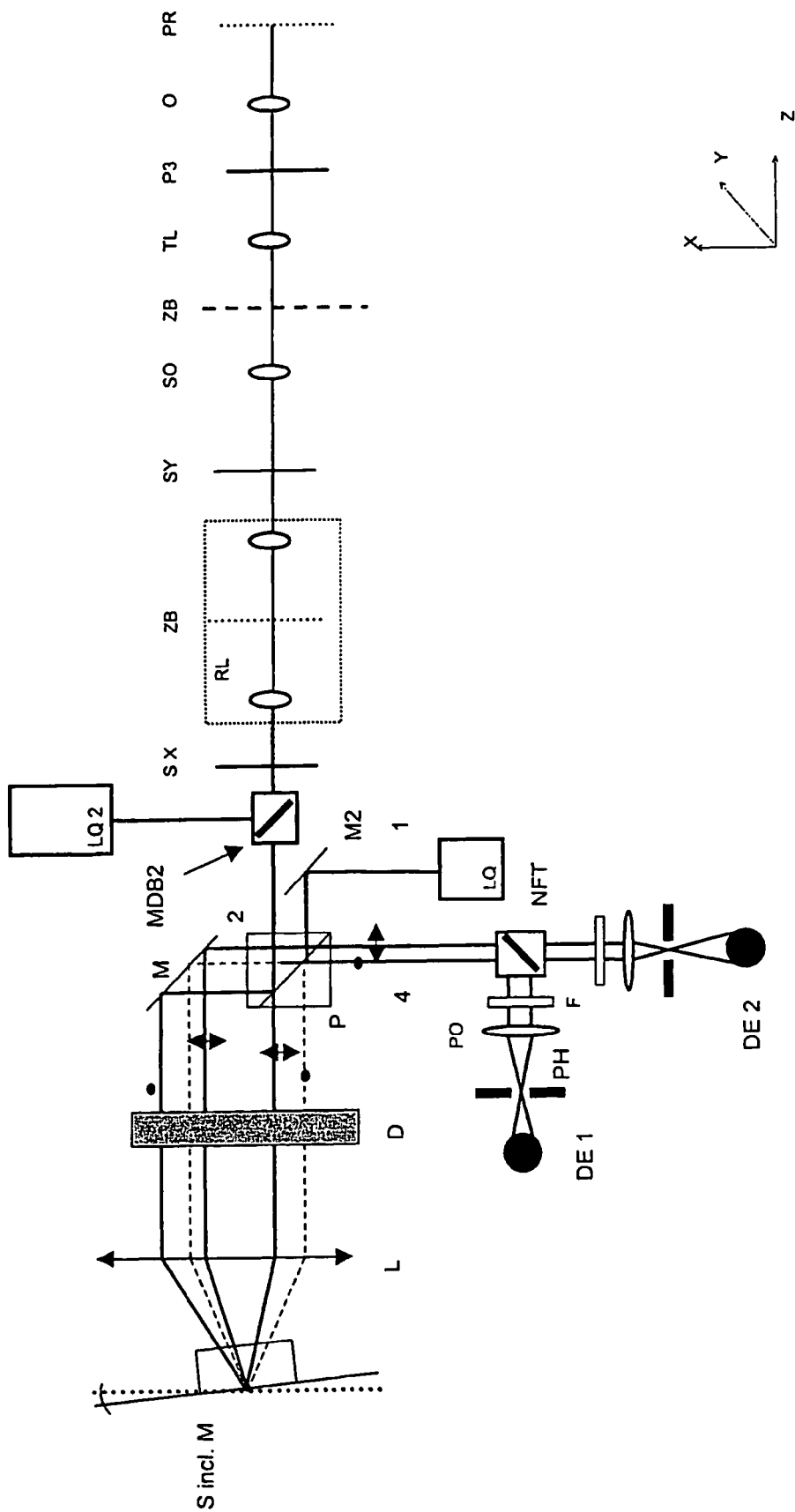
FIG. 13 is a schematic drawing of a composite arrangement of the inventive arrangement with detector arrangements DE1 and DE2, light sources LQ and LQ2, and imaging optics, according to the prior art.

FIG. 13 is a composite arrangement with detector arrangements DE1 and DE2 as well as light sources LQ and (unaffected) light source LQ2 as well as imaging optics in the direction of the specimen PR, according to the prior art. The detection can be descanned, partially descanned or non-descanned. Further, the arrangement can be used in a parallel confocal microscope with a perforated grid in the illumination and/or detection beam path.

The invention claimed is:

1. Device usable for changing at least one of the illumination light and the specimen light of a microscope with respect to at least one of its spectral composition and intensity, and for separating the illumination light from the specimen light, comprising:

first polarization means for spatially separating at least one of the illumination light and the specimen light of the microscope into radiation components of different polarization directions, first dispersion means for spectrally spatially splitting at least one radiation component downstream of the first polarization means, and for re-combining the at least one spectrally spatially split radiation component in an upstream direction, imaging optics for imaging the at least one spectrally spatially split radiation component from the first dispersion means onto a focal plane, means at the focal plane for changing the polarization direction of at least one part of the at least one spectrally spatially split radiation component, and tiltable reflection means for spatially shifting the radiation component having a changed polarization direction and reflecting it back through the imaging optics so that a variety of polarization directions reach different spots of the first dispersion means.

2. Method for changing at least one of the illumination light and the specimen light of a microscope including the device as claimed in claim 1, in an adjustable manner, comprising the steps of:

spatially separating at least one of the illumination light and the specimen light of the microscope into radiation components of different polarization directions using the first polarization means, reflecting and tilting at least one of the illumination light and specimen light using the reflecting means, spectrally spatially splitting at least one of the radiation components with the first dispersion means, and changing the polarization state of at least one part of the spectrally spatially split radiation component with the means for changing the polarization direction.

3. Method, as claimed in claim 2, further comprising the step of illuminating different specimen sites in a variety of ways by changing at least one of the intensity and spectral composition of the illumination light during image acquisition.

4. Method, as claimed in claim 2, wherein the microscope is a scanning microscope, and further comprising the step of carrying out one of a descanned, partially descanned, and non-descanned detection.

5. The device, as claimed in claim 1, wherein the means for changing the polarization direction comprises an SLM comprising actively controlled liquid crystal cells.

6. The device, as claimed in claim 1, wherein the microscope is a parallel confocal microscope and further comprises a perforated grid in at least one of the illumination and detection beam path.

* * * * *

UNITED STATES PATENT AND TRADEMARK OFFICE
CERTIFICATE OF CORRECTION

PATENT NO. : 7,605,976 B1 Page 1 of 1
APPLICATION NO. : 11/416455
DATED : October 20, 2009
INVENTOR(S) : Wolleschensky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 443 days.

Signed and Sealed this

Fifth Day of October, 2010

David J. Kappos
*Director of the United States Patent and Trademark Office*